(12) United States Patent
Nyholm

(10) Patent No.: US 7,761,174 B2
(45) Date of Patent: Jul. 20, 2010

(54) CONTROLLING A COMPUTER ARRANGED IN CONNECTION WITH A DENTAL UNIT

(75) Inventor: Kustaa Nyholm, Siuntio (FI)

(73) Assignee: Planmeca Oy, Helsinki (FI)

( * ) Notice: Subject to any disclaimer, the term of this patent is extended or adjusted under 35 U.S.C. 154(b) by 423 days.

(21) Appl. No.: 11/576,709

(22) PCT Filed: Oct. 5, 2005

(86) PCT No.: PCT/FI2005/050348
§ 371 (c)(1),
(2), (4) Date: Apr. 5, 2007

(87) PCT Pub. No.: WO2006/037862
PCT Pub. Date: Apr. 13, 2006

(65) Prior Publication Data
US 2007/0244581 A1 Oct. 18, 2007

(30) Foreign Application Priority Data
Oct. 5, 2004 (FI) .................................. 20041289

(51) Int. Cl.
*G05B 15/00* (2006.01)
*A61C 1/02* (2006.01)

(52) U.S. Cl. .......................................... 700/83; 433/99

(58) Field of Classification Search .................. 700/17, 700/83, 117, 180, 182; 433/98, 99, 100, 433/101; 348/66
See application file for complete search history.

(56) References Cited

U.S. PATENT DOCUMENTS

| 5,300,926 | A |  | 4/1994 | Stoeckl |
| 5,422,521 | A | * | 6/1995 | Neer et al. ................. 307/119 |
| 5,550,564 | A |  | 8/1996 | Cragun |
| 6,506,050 | B1 |  | 1/2003 | Steddin |
| 7,455,520 | B2 | * | 11/2008 | Sorensen et al. ............. 433/98 |
| 2001/0002725 | A1 |  | 6/2001 | Pollet et al. |
| 2004/0007907 | A1 | * | 1/2004 | DiRe ....................... 297/217.3 |
| 2007/0103270 | A1 | * | 5/2007 | Gmeinder et al. .......... 340/3.43 |
| 2007/0244581 | A1 | * | 10/2007 | Nyholm ...................... 700/83 |

FOREIGN PATENT DOCUMENTS

| DE |  | 196 22 323 C1 | 8/1997 |
| EP |  | 1 010 404 A2 | 6/2000 |
| WO | WO | 2004/080324 A1 | 9/2004 |
| WO | WO | 2005034784 A2 * | 4/2005 |

* cited by examiner

*Primary Examiner*—Ryan A Jarrett
(74) *Attorney, Agent, or Firm*—Cozen O'Connor

(57) ABSTRACT

A control arrangement and a method for controlling a computer comprised in a dental apparatus, said dental apparatus (100) comprising at least a computer (101) and its display (111) functionally connected to each other, a dental unit (102, 104) and a control arrangement which comprises control means (112, 116, 117) for controlling the functions of at least said computer and dental unit, wherein at least some of the control means (116) used to control said computer (101) are arranged in connection with said dental unit (102, 104) so as to allow the computer (101) to be controlled via the control means (116) arranged in connection with the dental unit (102, 104).

15 Claims, 2 Drawing Sheets

CONTROLLING A COMPUTER ARRANGED IN CONNECTION WITH A DENTAL UNIT

Figure 1:
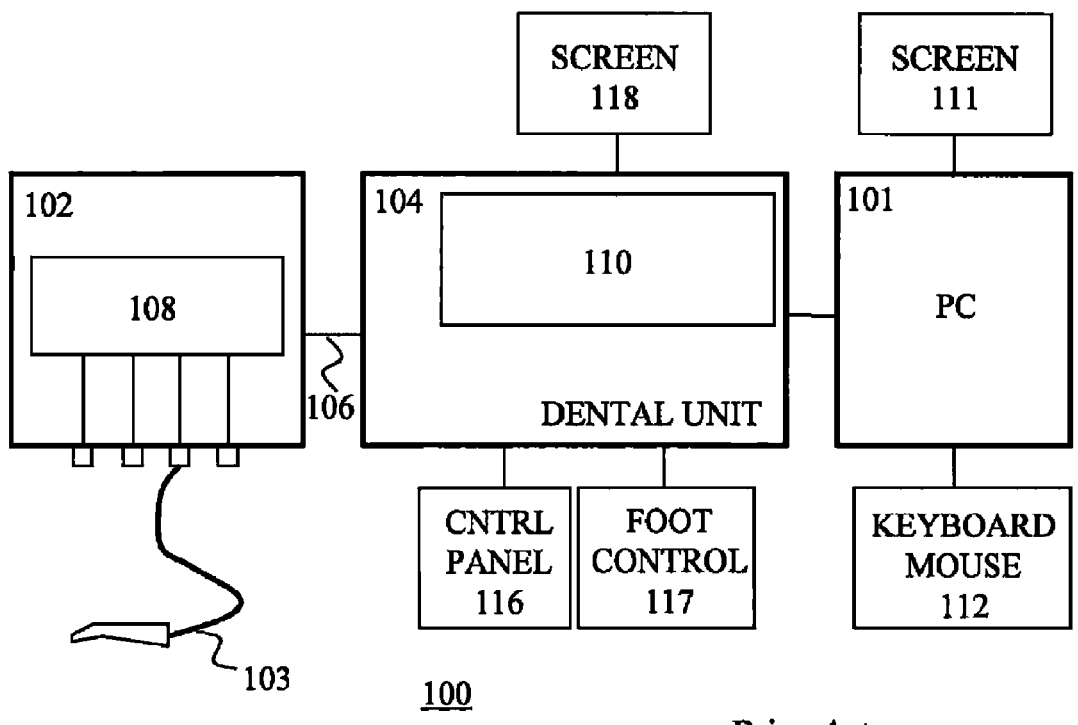

The invention relates to controlling of a computer arranged in connection with a dental unit, especially to easy-to-use, hygienic and ergonomic control of a computer in connection with dental care work. A dental apparatus in which the invention is applied comprises at least a computer and its display functionally connected to each other, the dental unit itself and a control arrangement, which comprises means for controlling functions of the aforesaid computer and the dental unit at least.

In all medical treatments, such as odontological treatments, disinfection of treatment instruments and environment is of high importance. The purpose of disinfection is to kill microbes and thus to make sure that the treatment environment and machines are safe for the patients. Disinfection can be carried out as thermal disinfection, for example by boiling an instrument or by sterilizing it in an autoclave, or as chemical disinfection, for example by wiping an instrument with suitable disinfectant or by soaking it in disinfectant solution. In disinfection, however, attention has to be paid to the material of the instrument. For example, not all plastic types withstand chemical disinfection as their surfaces may absorb disinfectant. Furthermore, some materials, such as some plastics, do not withstand high temperatures, either. Also many sensitive instruments do not endure autoclaving.

Disinfection is, however, a necessary measure in connection with daily dental care. Mere disinfection of instruments does not guarantee a hygienic environment for dental care, but also the dental unit itself and its controls should be so designed and manufactured that their surfaces can be easily disinfected and/or that they include detachable parts that endure autoclaving.

A computer placed in a dental care environment is typically controlled using a keyboard and a mouse. Instead of a mouse, e.g. a touch pad integrated with the computer may also be used. Dentists generally use the computer mainly for processing patient information and managing appointments. As digital imaging is gaining ground, the patient information comprises more often than before also photographs and x-ray images of patients. This image information can be processed by software on the computer and images can be presented on a display arranged in functional connection with the computer. In connection with treatments, dentists touch a patient with their hands and if also a computer is used in between, a hygienic risk arises as microbes, such as bacteria and viruses, may be transmitted from the control means of the computer to the patient through touch. In addition, as the computer is typically placed on a separate table or otherwise at a distance from the actual dental care working place, a person attending dental care always has to move from one working place to another in order to be able to use the computer in connection with the dental care event.

Cleaning and disinfecting a computer mouse or keyboard is difficult due to their shape and the materials used therein, whereby microbes may be transmitted from the controls further to patients through touch. This is quite problematic in connection with dental care because, when the patient's skin or mucous membranes are damaged, the body is exposed to microbes, which may cause e.g. infections. The controls used to control the computer may naturally be covered by a disposable or disinfectable protective cover, such as a plastic bag intended for the purpose, but then use of the control means is difficult and replacing or disinfecting the protective cover is relatively troublesome.

The object of the present invention is to develop an operating environment for a dental apparatus where the apparatus includes a computer and a display functionally connected to it in such a way that the computer may be controlled hygienically and, in case so desired, essentially from such a working place where the actual dental care, too, is attended. The object of the invention is achieved by the invention disclosed in the independent patent claims presented below, preferred embodiments of which being defined in the dependent claims.

The invention is based on a control arrangement in which the dental apparatus comprises a computer and its display operatively connected to each other, a dental unit and control means arranged in connection with it, said control means being arranged to be used for controlling the aforesaid computer arranged in the dental care environment. In this context, 'computer display' refers to a display device, which is used to display substantially all graphics generated on the computer (thus including, among other, the desktop, the possible windows, the cursor, etc.) and substantially in real time (i.e. in practice at least tens of times per second). 'The control means of a computer' on the other hand refers to means that can be used to control any computer program ordinarily found on the computer.

The means according to the invention for controlling a computer are preferably arranged to be used for controlling at least a dental unit as well, and preferably also for controlling e.g. a patient chair being located in connection with the dental unit. The control system of the dental apparatus may be implemented as connected to a computer so that the control signals from the control means are transmitted optionally, in other words, in accordance with a selectable operating mode either to the computer as computer control signals or alternatively either to the computer and/or to the dental unit as control signals for controlling the dental unit. Thus, the control means of the invention can be connected directly to the computer and, in accordance with its selectable operating mode, the control signals may be interpreted either as signals for controlling the computer, or they may be either arranged to be transmitted directly to the dental unit "as they are" or be regarded as control signals for a program provided on the computer for controlling the dental unit. Naturally, the computer may additionally be arranged to be operable via conventional computer control means as well.

By implementing the computer control means as a control panel being made up at least partially of a touch pad type solution, it will be relatively easy to integrate it with or connect it to the dental unit environment and to arrange its use hygienic. Thus, according to the invention, the control arrangement comprises means for moving and controlling a cursor on the computer display in response to touch by a pointing device, such as a pointing pen or finger, and in response to movement of it on the surface of the control panel provided in connection with the dental unit, which surface is substantially continuous and smooth and therefore easy to be wiped with disinfectant, or onto which surface is arranged to be fixed a detachable and disinfectable or disposable film, which upon wear can be replaced with a new one.

According to one preferred embodiment of the invention, at least a part of the control panel arranged to control the computer consists of a capacitive or resistive contact surface. Thus, according to a preferred embodiment of the invention, the control panel has been arranged to produce control information to the computer in response to pressing or sliding on the contact surface, thus producing a change in capacitance or resistance that is dependent on the point of contact. According to certain other preferred embodiments of the invention, the means for controlling the computer comprise a control panel arranged as an integrated part of the dental apparatus and to be used for controlling the functions of not only the computer but also the dental unit, whereupon the control panel may be arranged to comprise means that allow its operating mode to be changed between control of the computer and control of the dental unit. The control panel may be arranged to be used either merely as a contact surface controlling the cursor in both of the modes or such that, when controlling the computer, it functions as a touch pad controlling the cursor and, when controlling the dental unit, either as a touch screen including a touch pad, in which case the touch pad is made of transparent material and placed on a display screen displaying optional control functions for controlling a dental unit, or as a surface whereto push buttons or touch keys have been arranged via which control signals can be transmitted to the dental unit when the control panel is in the dental unit control mode. Further, according to one preferred embodiment of the invention, the surface of the control panel may also be arranged to comprise different areas such that one area is arranged to be used as a touch pad for controlling a computer and another area for controlling a dental unit, in which case the aforesaid another area may be implemented optionally either e.g. also as a touch pad or as a push button keyboard or touch key keyboard or by touch screen technology.

The invention allows the control arrangement of a computer used in dental care environment to be implemented as easily cleanable and disinfectable between or even during treatments and in such a way that the computer can be operated without having to move to a working place provided specifically for use of the computer, whereby use of the computer in connection with dental care work is considerably easier and more hygienic than in prior art solutions. As the computer can also be operated while wearing protective gloves, this facilitates controlling of the computer in connection with treatments. One is able to quite freely arrange placement of the control arrangement implemented as a touch pad in a dental care environment and it can be placed in an ergonomically advantageous location, such as e.g. integrated as part of some surface of the dental unit, such as a cover of an instrument table.

Figure 2:
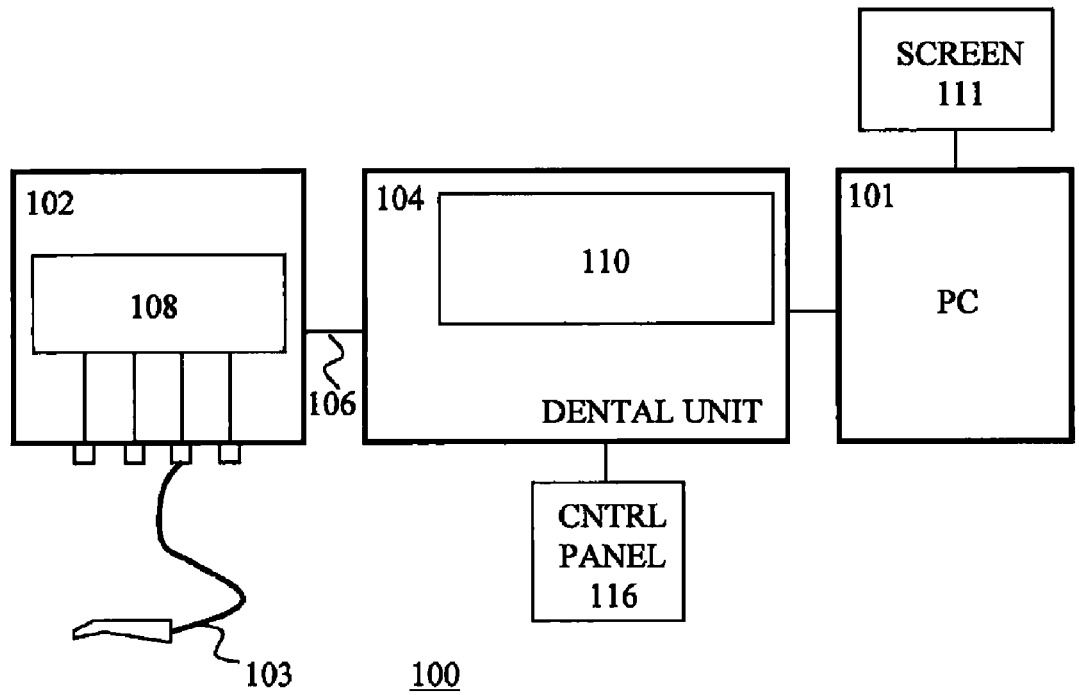

In the following, the invention and its preferred embodiments will be described in more detail and also with reference to the attached figures, of which FIG. 1 presents a block diagram representing a prior art dental unit configured to be in functional connection with a computer, FIG. 2 presents a block diagram of a control arrangement according to the invention for controlling a computer comprised in a dental apparatus, and FIGS. 3a-3d present some control panels according to preferred embodiments of the invention for controlling a computer, on the one hand, and a dental unit, on the other hand.

A block diagram representing a prior art dental apparatus (100) is presented in FIG. 1, which comprises a dental unit (102, 104) and a computer (101) functionally connected to it. In this context, dental unit refers to a device to which it is possible to connect one or more instruments (103) used in dental treatment, the dental unit being arranged to supply e.g. electric power, water and/or compressed air to said instruments. The dental unit typically comprises an instrument table (102), a body part (104) and a cable duct (106) that connects the two. The instrument table (102) typically comprises an electronics/pneumatics unit (108) arranged to be used for controlling the instruments (103), while the body part (104) comprises an electronics/pneumatics unit (110) of its own. The instruments (103) may be connected to the instrument table (102) via mutually identical instrument connectors C, whereby the dental unit is arranged to identify the instrument or instrument type in use at the time so that in response to connection of a given identified instrument (103) to an instrument position C in question, the electronics/pneumatics unit (108, 110) adjusts the physical variables required for operating that instrument in accordance with requirements of that particular instrument. The cable duct (106) contains the electric conductors and signal conductors as well as the lines for transfer of water and air.

Using the controls (116), (117) functionally connected to the dental unit (102, 104), such as the keyboard (116) and the foot control (117), control commands may be transmitted to the electronics/pneumatics unit (110) of the body part (104) of the dental unit and/or directly to electronics/pneumatics unit (108) of the instrument table (102). There may also be arranged in connection with the dental unit a display (118) of the dental unit, in which case e.g. patient images stored in the computer (101) memory may be transmitted to it for display or the display may be used as controlled via the controls (116, 117) of the dental unit e.g. to present various status information of the dental unit or as a means to control functions of the dental unit itself, such as for transmitting control commands for adjusting the operation of the instruments (103) or for producing settings related to their operation, and/or e.g. for controlling movements of a patient chair placed in connection with the dental unit. The electronics/pneumatics unit (108, 110) may comprise a digital data processing unit, such as a microprocessor, to which control information produced by the controls (116, 117) is transmitted as a control signal.

Functionally connected to the computer (101) there is a computer display (111) and its control means (112), which may consist of e.g. a keyboard and a mouse. Between the computer (101) and the dental unit (104) there is arranged a data transfer link (107), over which e.g. information relating to patients or to the dental unit may be transmitted from one machine to the other.

FIG. 2 presents in a simplified manner a solution according to the invention for controlling, in connection with dental care operation, a computer (101) arranged in connection with a dental unit (102, 104), wherein there is arranged control means (116) in connection with the dental unit for controlling at least the computer (101). These control means are preferably implemented at least partly as a control panel (116) comprising a touch pad, which is arranged to produce control information, such as control signals, for the computer (101) in cooperation with the display (111) of the computer (101) in response to the contact surface of the touch pad being pointed with a pointing device, such as a pointing pen or a finger. 'Touch pad' here refers to a contact and motion sensitive user interface for entering control information. The user enters control information, such as a command, by moving and touching/pressing e.g. by a finger or some other pointing device the contact-sensitive area, i.e. the contact surface of the touch pad. The touch pad can be used like a mouse controller by moving the pointing device on the contact surface and pressing ("clicking") it when the cursor is located at a desired position on the display (111) of the computer (101). In the dental operating environment, it is advantageous to use a touch pad as a computer control means because a touch pad can be effortlessly cleaned and disinfected thanks to its simple shape and the material it is made of.

One touch pad applicable for use in the invention is e.g. a touch pad comprising a resistive or capacitive contact surface that is able to recognize both motion and pressure. Such a touch pad typically consists of passive thin insulating and electrically conductive layers one on top of the other, the capacitances and/or resistances between the layers changing as the surface is touched. The point of contact on the touch pad can be determined by measuring the capacitance or resistance values of the surface of the touch pad. A contact surface operating on the resistive principle has the advantage that it works well even when touched with protective gloves, which may become a problem in connection with a contact surface operating on the capacitive principle. The touch pad may also consist of two line electrode matrices positioned in a rectangular configuration relative to each other and separated by an insulator. In this case, touching the pad with a finger or the like changes the capacitance between the lines of the matrix, which can be detected as position information.

According to a preferred embodiment of the invention, the contact surface of the touch pad is so implemented that it withstands chemical disinfection. Exposure of the surface to disinfectant may be reduced by attaching onto the contact surface a thin, detachable and preferably disinfectable or disposable film through which recognition of a touch may take place and which can be replaced with a new one upon wear.

The touch pad can be connected to the dental unit through a connection interface and placed to form part of some surface of the dental unit, such as part of the cover of the instrument table. Correspondingly, the touch pad may be arranged in connection with the patient chair, such as to the lower surface of the backrest. The touch pad of the invention may also be implemented as a separate auxiliary device, which may be mechanically connected to the dental unit by e.g. an arm, or by providing for it a separate support, such as a support leg, that can be placed freely in the dental care environment but, anyhow, by connecting the control panel functionally to the dental unit. Regarding placement of the control panel it is possible to consider ergonomics e.g. by placing the panel as reachable by hand in the substantial vicinity of the dental care working place. The invention also enables an arrangement where the user of the dental unit does not e.g. need to see which key or symbol of the control means his finger may be touching, thus allowing the control panel to be placed ergonomically or otherwise practically even in a location that cannot be directly seen from the dental care working place.

The dental apparatus (100) according to the invention is shown in a simplified manner in FIG. 2 expressly from the point of view of how the computer (101) comprised in the apparatus can be controlled according to the invention. Applying the invention does not mean, however, that the computer (101) could not be arranged to be controlled, in addition, by the traditional prior art computer control means (112) as well. Implementing of the invention does not prevent controlling of the dental unit according to prior art, either. On the other hand, according to the invention, the display (111) of the computer (101) may be placed anywhere in the dental care environment, for example by attaching it physically to the dental unit itself. The arrangement of the invention may be implemented using either two displays, in other words, so that both the computer (101) and the dental unit (102, 104) have their own displays (118, 111), or by altogether omitting the display (118) of the dental unit and providing a possibility to use the display (111) of the computer to display information obtained e.g. from the dental unit as well. The control information can be arranged to be brought from the control panel (116) to the computer (101) e.g. via a mouse interface already available in the computer (101) or it can be received via a data transfer arrangement and the computer (101) can be provided with driver software which then emulates the mouse to the computer (101).

Figure 3A:
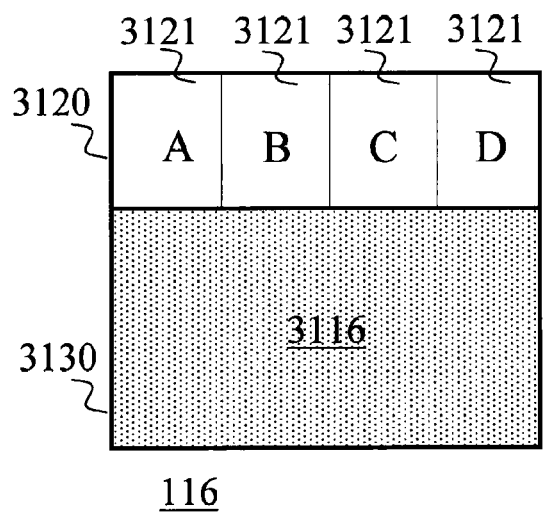

According to a preferred embodiment of the invention, the control means (116) provided in connection with the dental unit for controlling the computer (101) is also arranged to be used for controlling the dental unit. FIGS. 3a-3d show control panel solutions (116) that can be used to implement this preferred embodiment of the invention. FIG. 3a presents a solution where two functionally different areas are arranged to the control panel (116), the first one (3120) of which being arranged to transmit control signals to the dental unit (102, 104) and the second one (3130) to the computer (101). In the solution according to FIG. 3a, the upper part (3120) of the control panel (116) is divided into push buttons (3121) sending signals to the dental unit and the lower part (3130) forms a contact surface (3116) controlling the cursor on display (111) of the computer (101), whereas the control panel (116) according to FIG. 3d consists completely of such a surface controlling the cursor except that one area (3110) has been arranged thereto by which the operating mode of the control means (116) may be changed from control of the dental unit to control of the computer and vice versa. Naturally, such a change of the operating mode of the controls can be arranged to be made from elsewhere than from the control means itself as well, in which case its entire active surface can be arranged to function as a contact surface (3116) of the touch pad controlling the cursor. On the other hand, in the solution according to FIG. 3a, the area (3120) containing push buttons (3121) used to control the dental unit may also be implemented by some other technology than by push buttons, for example as touch keys, as a touch screen or as a second contact surface separated from the lower part (3130) of the control panel (116).

Figure 3B:
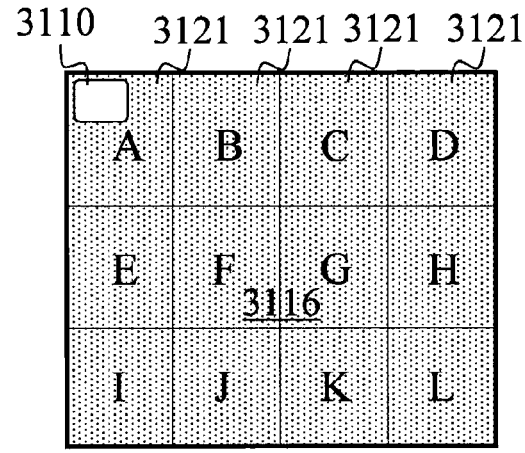
Figure 3C:
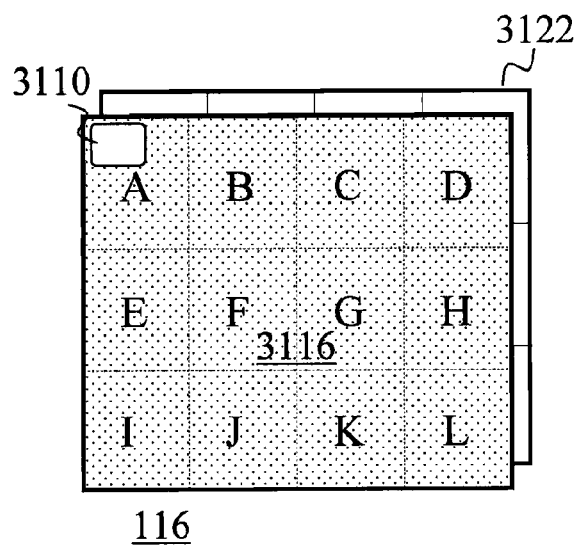
Figure 3D:
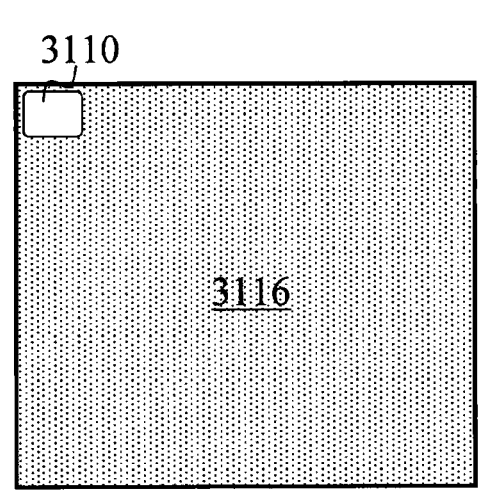

With respect to FIGS. 3b and 3c, they show solutions in which the control functions of the computer, on the one hand, and those of the dental unit, on the other hand, are arranged as if one on top of the other. In this case, e.g. in the solution according to FIG. 3b, the control means (116) of the invention functions in the dental unit mode as a touch button keyboard (N×3121) as known in prior art, whereas in the computer mode it functions as a contact surface (3116) controlling cursor movements on the display (111) of the computer (101). The symbols in the touch buttons (3121) to be used according to prior art may be e.g. printed on the material used in the touch pad.

The controls according to FIG. 3c functions like the controls according to FIG. 3b when in the computer mode, but instead of push button technique the control of the dental unit is implemented by using touch screen technology, where a display (3122) is arranged under the transparent contact surface (3116) of the control panel (116) for displaying symbols controlling operation of the dental unit. Especially the embodiment of the invention according to FIG. 3b provides freedoms of choice regarding placement of the control means of the computer, as from the technical point of view it is relatively easy to implement even on a curved surface of a dental unit, if desired. Such an embodiment of the invention can also be implemented in a relatively simple manner by replacing the push button keyboard generally used in dental units with a touch pad according to the invention, as it is then possible to utilize the mechanical and electronic solutions already available in the dental unit—or in some cases even almost as such as an accessory for controlling the computer, e.g. if the button technology used in the dental unit is or functionally approaches touch key technology. Correspondingly, if the invention is applied in a dental unit in which touch screen technology has already been applied for controlling the dental unit, corresponding advantages are naturally also gained in the embodiment according to FIG. 3c.

A preferred embodiment of the invention, in which both the computer and the dental unit are controlled by a touch pad solution in which no buttons/symbols are used at all but all information related to control is visible on a display, and the cursor presented on it is controlled via the control panel, enables relatively free placement of the control panel in the dental care environment because one is then able to arrange it even in a location whereto the user does not have to see in order to perceive, which control command corresponding the symbol one is about to give. The display can be arranged to present graphics, symbols and/or alphanumeric signs relating to control of both the computer and the dental unit, but also information relating e.g. to control or the like of the patient chair or some other device including to the dental care environment. In this case it is possible to arrange the control panel, too, to include e.g. three different operating modes, three distinct operating areas, or correspondingly to allow in some other way transmitting of control commands to that other device in question as well.

It is obvious to a man skilled in the art that the invention and its embodiments are not limited to the examples described above, but that e.g. as technology advances, the inventive concept defined in the claims below can also be implemented in other ways besides those described above.

The invention claimed is:

1. Control arrangement for controlling a computer comprised in a dental apparatus, said dental apparatus comprising a computer and a display functionally connected to each other, a dental unit and a control arrangement which includes a control means for controlling functions of said computer and said dental unit, said control means being arranged in connection with said dental unit as bi-functional such that said control means is arranged for transmission of signals directly to the dental unit for controlling said computer and said dental unit, wherein said control means arranged for transmission of signals directly to the dental unit is arranged to control the computer by transmitting control information from said control means for controlling a cursor to be presented on the display of the computer.

2. Control arrangement according to claim 1, wherein said control means comprises a touch pad having a contact surface and is arranged to transmit control information for controlling operation of the cursor presented on the display of the computer in response to moving and touching operations performed with a pointing device on said contact surface of said touch pad.

3. Control arrangement according to claim 1, wherein said control means is arranged to form a part integrated to the dental unit.

4. Control arrangement according to claim 3, wherein said control means is arranged to form a part integrated to an instrument table to said dental unit, or to a backrest of a patient chair.

5. Control arrangement according to claim 1, wherein control information to be transmitted from said control means to the computer is arranged to be brought to the computer via a mouse interface, or via a data transfer arrangement in such a way that a driver software is arranged in the computer which is arranged to emulate to the computer a mouse controller in accordance with the control information received via the said data transfer arrangement.

6. Control arrangement according to claim 2, wherein said bi-functionality of the control means is implemented in such a manner that the operating mode of said contact surface has been arranged to be changeable from computer control mode to dental unit control mode.

7. Control arrangement according to claim 2, wherein said bi-functionality of the control means is implemented in such a manner that said contact surface is arranged to control the cursor presented on a display also in the dental unit mode in response to moving and touching operations performed by a pointing means on the contact surface of said touch pad, whereby in said dental unit mode graphics, symbols and alphanumeric signs which relate to controlling of the dental unit has been arranged to be presented on said display.

8. Control arrangement according to claim 2, wherein said bi-functionality of the control means is implemented by arranging said contact surface to function, in the dental unit mode, as such a contact surface which is based on touch screen, touch button or touch key technology.

9. Control arrangement according to claim 2, wherein an area is arranged to the said contact surface, which is arranged to transmit a control signal of change of the operating mode of the control means from computer mode to dental unit mode and vice versa.

10. Control arrangement according to claim 2, wherein said contact surface comprises a capacitive or a resistive contact surface.

11. Control arrangement according to claim 2 wherein said bi-functionality of the control means is implemented by arranging the said control means to comprise the contact surface in which a first area has been arranged for transmitting signals to be used to control the computer and a second area for transmitting signals to be used to control the dental unit.

12. Control arrangement according to claim 11, wherein said first area is arranged to function as said contact surface and the said second area is implemented either by push button/touch key technology or by touch screen technology or as a second contact surface.

13. A method for controlling a computer which is arranged to be a part of a dental apparatus, said dental apparatus comprising at least a computer and its display connected to each other functionally, a dental unit and a control arrangement which includes a control means for controlling functions of said computer and dental unit, wherein said control means is arranged in connection with the dental unit and wherein said dental unit and said computer are controlled via said control means so that said control means transmits signals directly to the dental unit, wherein controlling said computer includes using said control means for controlling a cursor to be presented on the display of the computer.

14. A method according to claim 13, wherein control information to be transmitted from said control means to the computer is passed to the computer via a mouse interface, or via a data transfer arrangement in such a way that the computer is arranged to include a driver software which is arranged to emulate a mouse controller to the computer in accordance with the control information received via said data transfer arrangement.

15. A method according to claim 13, wherein said computer is controlled via a touch pad which comprises a contact surface by controlling operation of a cursor presented on the display of the computer.

* * * * *